United States Patent
Rea et al.

(10) Patent No.: US 8,467,844 B2
(45) Date of Patent: Jun. 18, 2013

(54) ELECTRODE FOR PROLONGED MONITORING OF LARYNGEAL ELECTROMYOGRAPHY

(75) Inventors: James Lee Rea, Ventura, CA (US); Stephen W. Blakely, O'Fallon, MO (US)

(73) Assignee: Neurovision Medical Products, Inc., Ventura, CA (US)

( * ) Notice: Subject to any disclaimer, the term of this patent is extended or adjusted under 35 U.S.C. 154(b) by 298 days.

(21) Appl. No.: 12/887,427

(22) Filed: Sep. 21, 2010

(65) Prior Publication Data

US 2011/0071379 A1    Mar. 24, 2011

Related U.S. Application Data

(60) Provisional application No. 61/244,402, filed on Sep. 21, 2009.

(51) Int. Cl.
*H01R 43/00* (2006.01)
(52) U.S. Cl.
USPC ............. 600/380; 600/393; 600/546; 29/825
(58) Field of Classification Search
USPC ........................................................ 600/380
See application file for complete search history.

(56) References Cited

U.S. PATENT DOCUMENTS

| | | | |
|---|---|---|---|
| 3,326,207 A | 6/1967 | Egan | |
| 4,461,304 A * | 7/1984 | Kuperstein | 600/378 |
| 4,890,623 A * | 1/1990 | Cook et al. | 600/374 |
| 5,125,406 A * | 6/1992 | Goldstone et al. | 600/380 |
| 6,095,987 A | 8/2000 | Shmulewitz et al. | |
| 6,292,689 B1 | 9/2001 | Wallace et al. | |
| 6,401,001 B1 | 6/2002 | Jang et al. | |
| 6,460,958 B2 | 10/2002 | Kubo et al. | |
| 2001/0017085 A1 | 8/2001 | Kubo et al. | |
| 2003/0100824 A1 | 5/2003 | Warren et al. | |
| 2006/0095032 A1 | 5/2006 | Jackson et al. | |
| 2009/0227885 A1 | 9/2009 | Lowery et al. | |

FOREIGN PATENT DOCUMENTS

| | | |
|---|---|---|
| WO | WO2004/016438 | 2/2004 |
| WO | WO2006/105121 | 10/2006 |

OTHER PUBLICATIONS

Shaw-Klein, L., "Material Selection When Printing Functional Traces on Medical Devices", EMEDT, p. 1-5, May 2010, Sep. 13, 2010 <http://www.emdt.co.uk/article/material-se.

(Continued)

*Primary Examiner* — Lee S Cohen
(74) *Attorney, Agent, or Firm* — Koppel Patrick Heybl & Philpott; Michael J. Ram

(57) ABSTRACT

Laryngeal surface electrodes are devices designed to hold a conductive surface against the vocal cords in order to pick up small electrical signals from the muscle known as electromyographic signals. Several embodiments of a laryngeal electromyography tube include a conductive electrode surface that is painted, screen printed or otherwise applied directly onto the body of an endotracheal tube, such that the final device has no raised surfaces which can injure the vocal cords. These endotracheal tube with integral laryngeal surface electrodes can be safely used placed for prolonged, continuous monitoring during surgery, after surgery and during intensive care treatment intubation without a need to remove and replace the tube at these various stages of treatment. In one embodiment, one electrode contacts the vocal cords and a second electrode contacts the tongue.

7 Claims, 6 Drawing Sheets

OTHER PUBLICATIONS

"The most precise way of applying flowable materials to surfaces", MicroPen Technologies, p. 2-3, Sep. 13, 2010 <http://www.micropen.com/Micropenning/overview.php>.

How It Works: MicroPen Technologies Precisely write patterns with any . . . , Micropen Technologies, p. 1-3, Sep. 13, 2010, <http://www.micropen.com/Micropenning/how_it_works.

Flowable Materials: MicroPen Technologies, Precisely write patterns wit . . . , p. 1-3, Micropen Technologies, p. 1-3, Sep. 13, 2010, <http://www.micropen.com/Micropenning/flo.

"113-09 Electrically Conductive Ink", Creative Materials, Inc., p. 1, Jan. 1, 2010 <www.creativematerials.com>.

"117-43 Screen-Printable Waterborne Medical Grade Conductive Ink & Coating", Creative Materials, Inc., p. 1, Feb. 9, 1996, <www.creativematerials.com>.

"119-10 Pad Printable Electrode Ink", Creative Materials, Inc., p. 1, Apr. 30, 1997, <www.creativematerials.com>.

"Developments in Conductive Ink", Vorbeck Materials, p. 1-3, Sep. 14, 2010, <http://www.vorbeck.com/news.html>.

Micropen Technologies, p. 1, 2010, <http://www.micropen.com/Resources/InkSubstrateCompatibility.pdf>.

Pieper, Carl F. et al., "Experience with Kapton-Based Bipolar Electrode Arrays Used During Computerized Intraoperative Mapping", J Cardiovascular Electrophysiology (Abstract), Dec. 1990.

* cited by examiner

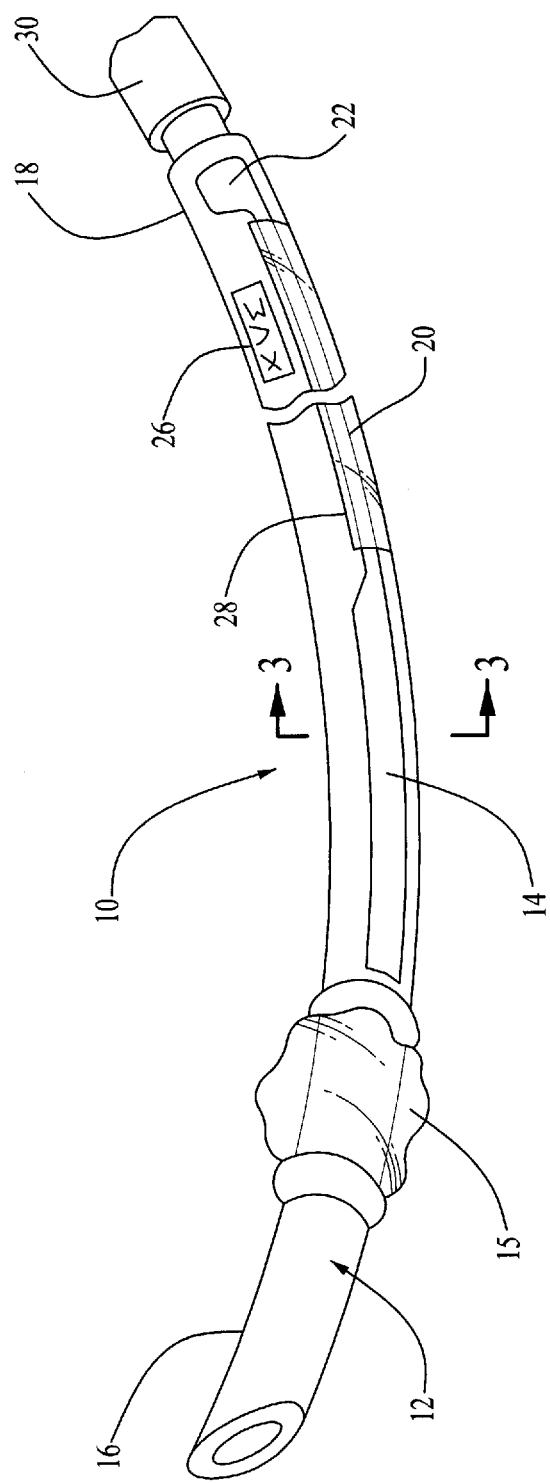

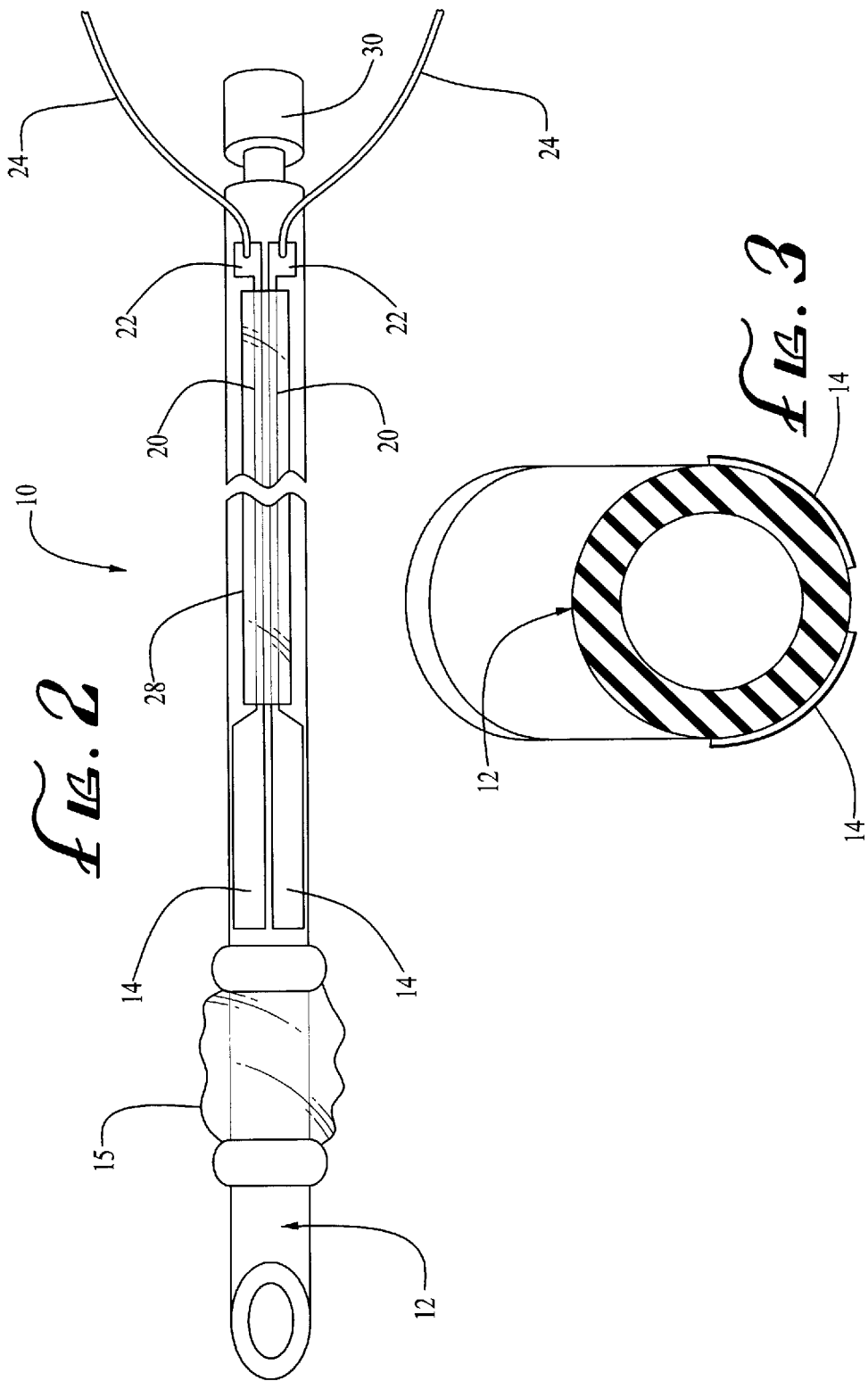

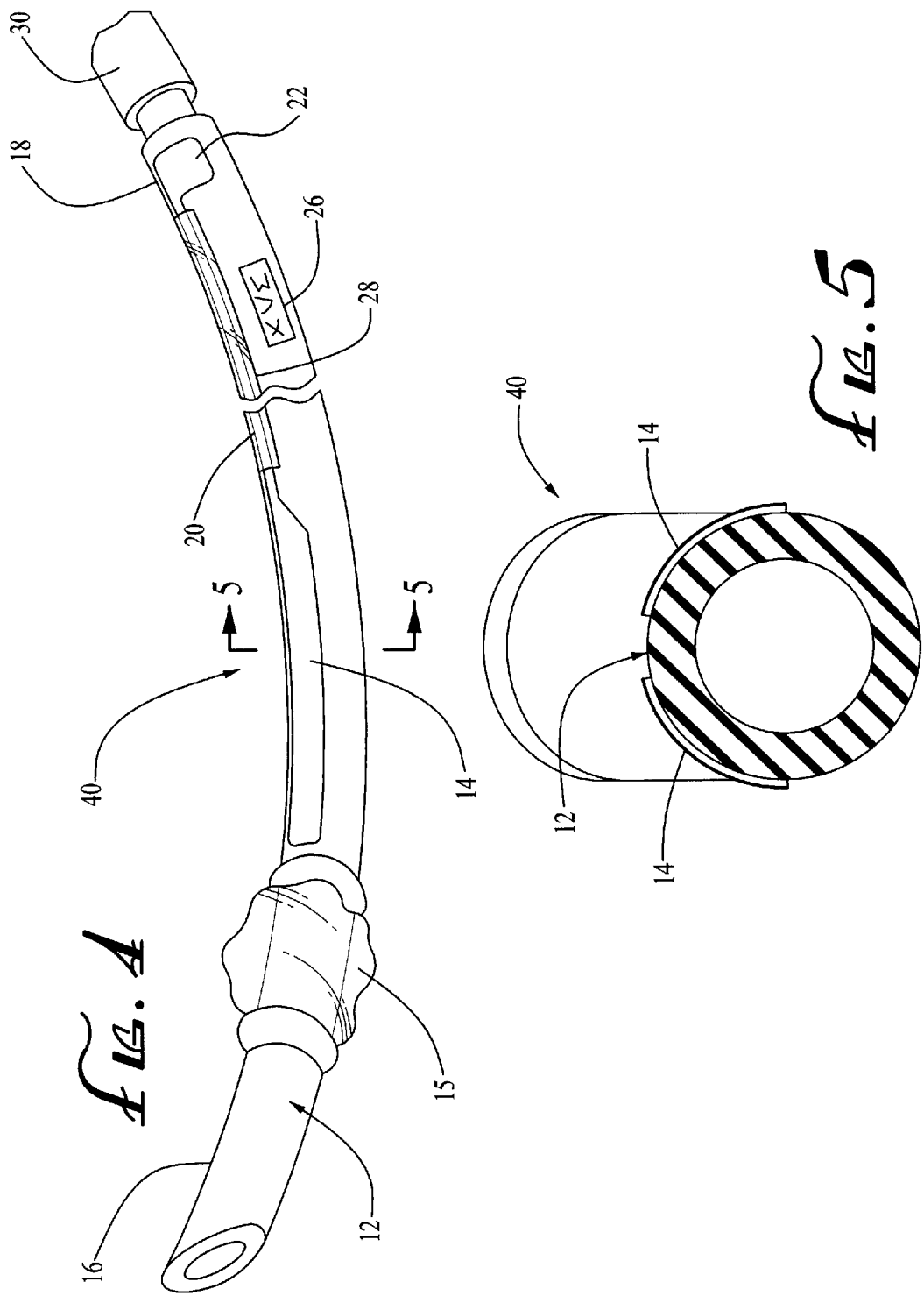

ELECTRODE FOR PROLONGED MONITORING OF LARYNGEAL ELECTROMYOGRAPHY

This application claims benefit of U.S. Provisional Application Ser. No. 61/244,402, filed Sep. 21, 2009.

BACKGROUND

Endotracheal tubes are commonly used during anesthesia and intensive care in order to support respiration of a human patient who may be unable to breathe without the use of mechanical breathing support devices. Endotracheal tubes may have electrodes on the surface thereof for performing laryngeal electromyography and monitoring the recurrent laryngeal nerve during medical procedures. These electrodes on the endotracheal tube, referred to as laryngeal surface electrodes, are currently used in various surgical procedures to provide monitoring of the electromyographic signals from the muscles of the vocal cords, or larynx. The electrical signal typically transmitted to the tissue and detected using electronic monitoring equipment is generally from about 10 microvolts to about 2 millivolts. This monitoring procedure allows the surgeon to intermittently stimulate the nerves, for example nerves connected to the vocal cord muscles, with a nerve stimulator, and to electronically evaluate, or view on a video monitor, the muscle electrical responses, thereby giving the surgeon an indication of the location and physiologic integrity of these nerves during performance of a surgical procedure. This is particularly useful in Thyroidectomy and Para-thyroidectomy operations. In addition, laryngeal monitoring has been found to be of clinical value in certain neurosurgical and orthopedic surgical procedures such as Anterior Cervical Discectomy and Posterior Fossa Craniotomy. Also, with prolonged intubation and airway ventilator support, such as is provided in an intensive care unit for certain medical conditions, such as chest trauma, pneumonia, or chronic lung disease, medical practitioners would benefit from being able to evaluate laryngeal electromyography on an ongoing basis to evaluate the depth of sedation and the patient's status to determine if the airway support is still required or whether the endotracheal tube can be removed.

Currently, it is common practice to monitor laryngeal electromyography using laryngeal electrodes (the electrical signal pickup surfaces used to collect the muscle signals) which are either adhesively secured to the surface of the endotracheal tube or are embedded into the tube surface during the manufacture of the endotracheal tube. Both of these methods involve the addition of components to the endotracheal tube which are not commonly incorporated into this device such as metallic plates, adhesives, lead wires, and structural elements resulting in raised portions on the smooth physical profile of the endotracheal tube surface. Additionally, these devices can also introduce structures into the vicinity of the larynx and can cause injury to the vocal cords. For these reasons, the manufacturers of all currently available laryngeal surface electrodes do not recommend continuous laryngeal electrode placement for monitoring purposes in excess of eight hours. The surgeon and anesthesiologist are therefore required to remove the dedicated endotracheal tube with attached electrode and reintubate the patient with a standard, non-electrode endotracheal tube prior to moving the patient to the recovery room or ICU for prolonged respiratory support. This entails the risk of a separate, second airway manipulation and deprives the physician of valuable information which is provided by prolonged and continuous laryngeal monitoring.

Additionally, because the components of the electrodes in current embodiments of attachable or integrated endotracheal tube electrodes are different in structure and type to standard endotracheal tube components, they create a zone of stiffness that does not allow, or retards, flexing of the endotracheal tube when placed in its desired position, namely in a semi S-curve configuration extending for the length of the electrode element. By constructing the part of the endotracheal tube electrode that is inside the patients mouth, pharynx, and larynx using components which are flexible, rather than rigid, such as described herein below, the endotracheal tube electrode are located for optimal signal collection and minimal negative effects on the surrounding laryngeal tissue, subject to other constraints caused by the other materials used to form the laryngeal tube.

SUMMARY

An device for prolonged laryngeal electromyography monitoring comprises, in a preferred embodiment, an endotracheal tube, which can be a standard commercial endotracheal tube, with electrodes and electroleads screen printed on the exterior surface thereof using a conductive ink or paint, in a pattern such that it is optimized for positioning in the larynx and collection of electrical signals from the muscles and nerves comprising the vocal cords. The current most commonly used endotracheal tube is made of polyvinylchloride (PVC) or Silastic™. These tubes may also be imprinted with lettering to designate the manufacturer, size, serial number, scaled length to indicate depth of penetration from the lips, and other written precautions and information such that the manufacturer and regulatory agencies deem appropriate. As such the endotracheal tube laryngeal surface electrode incorporates imprinted patterns which provide conductive electrode plates on the surface without adding any additional structure or materials to the standard endotracheal tube other than the conductive ink or materials applied to the surface to form the electrodes. In a first embodiment the conductive paint or printing ink used consists of a liquid solution or suspension of conductive material, such as a silver, gold, silver chloride, or various other conductive materials, such that when the solution dries or otherwise solidifies it forms a firmly adherent, thin, electrically conductive layer on the body of the tube. In an alternative embodiment, the conductive material may sprayed on the tube surface in the desired pattern to form continuous conductive patterns on the surface.

An object is to provide a laryngeal surface electrode on an endotracheal tube where the electrode plates do not raise the profile of the body of the tube so as to create a safety hazard from possible trauma to the vocal cords.

Another object is to provide a laryngeal surface electrode that can be used for prolonged intubation and prolonged contact of the electrode surfaces with the vocal cords without raising concerns of unsafe condition or traumatic injury to the vocal cords resulting from separation or delamination of the electrode structure from the endotracheal tube surface.

Another object is to provide a laryngeal surface electrode that can remain indwelling during the entire surgical procedure and intensive care period of treatment of the patient, thereby providing the medical practitioner the ability to review laryngeal electromyography monitoring to assess the depth of sedation during treatment or surgery allowing the assessment of the patients laryngeal motor power during the decision process leading to removal of respirator support and of the endotracheal tube.

An additional object is to provide a PVC laryngeal surface electrode with the electrodes painted, printed or sprayed on the surface thereof, thereby providing the flexibility of the PVC material throughout the length of the device. The painted, printed or sprayed on electrodes does not create a zone of stiffness anywhere along the length of the endotracheal tube, and particularly near the vocal cords The flexibility of the endotracheal tube is not constrained or otherwise compromised by incorporation of a separate electrode structure on the tube surface. In addition, the traces, also referred to as leads are likewise applied to the surface of the tube, allowing the lead wires to be attached near the top of the tube (the external end of the endotracheal tube), and outside the patient's mouth, thus eliminating additional clutter in the patient's pharynx and an additional possible source of injury to the vocal cords with malpositioning of the device.

An additional object is to provide a laryngeal surface electrode that can be manufactured with electrode surfaces and multiple electrodes for various different applications and endotracheal tube sizes so as to provide a dual channel structure with four electrode plates or pediatric (single electrode) versions.

A further object is to provide an electrode that is economical to manufacture, efficient to use, and particularly well adapted for prolonged use. Other objects and advantages of this invention will become apparent from the following description taken in connection with the accompanying drawings wherein are set forth, by way of illustration and example, certain embodiments of this invention. The drawings constitute a part of this specification and include exemplary embodiments and illustrate various objects and features thereof.

BRIEF DESCRIPTION OF THE DRAWINGS

FIG. 1 is a perspective view of an embodiment of an electrode for prolonged monitoring of laryngeal electromyography incorporating features of the invention.

FIG. 2 is a bottom view of the embodiment of FIG. 1.

FIG. 3 is a cross sectional view of the embodiment of FIG. 2 taken along line 3-3 of FIG. 2.

FIG. 4 is a perspective view of a second embodiment of an electrode for prolonged monitoring of laryngeal electromyography incorporating features of the invention.

FIG. 5 is a top view of the embodiment of FIG. 4.

DETAILED DESCRIPTION

Figure 6:
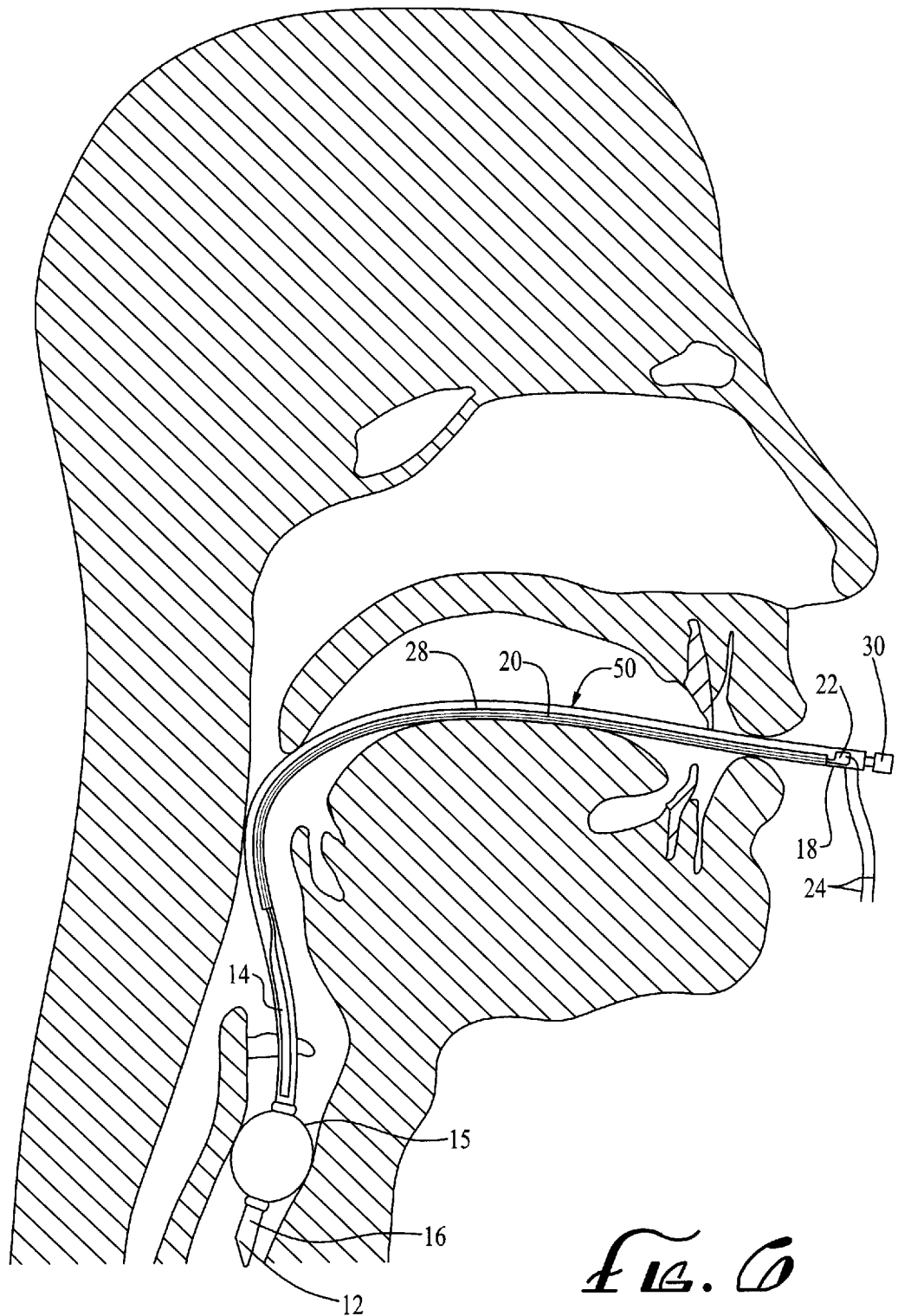
FIG. 6 is a view showing the endotracheal tube of FIG. 4 placed within the trachea with the electrode plates adjacent the vocal cords.

Certain features of the device described and shown herein are enlarged in the Figures for clarity and may be smaller and thinner then depicted in the Figures. In addition, other components, which may or may not be transparent, are shown as transparent so that the locations of the underlying features are readily visible.

With reference to FIGS. 1-3, a laryngeal electromyography tube 10 for use in prolonged laryngeal electromyography monitoring is shown. The laryngeal electromyography tube 10 comprises an endotracheal tube 12 upon which conductive electrode plates 14 are imprinted on the linear body of the tube 12 from a point adjacent to the endotracheal tube balloon 15, shown as a transparent material, at the distal end 16 of the tube 12. The length of the electrode plate 14 is chosen so as to be appropriate for clinical use and electrical signal capture. Extending away from the plates 14, toward the proximal end 18 of the laryngeal electromyography tube 10 is a conductive trace 20 which terminates on a conductive pad 22 for attachment of a lead wire 24. The lead wire 24 is of a length suitable to allow the laryngeal electromyography tube 10 to be attached to externally located electro-physiologic devices (not shown) such that the user may capture and evaluate the signals from the vocal cord received by the plates 14.

A typical endotracheal tube has a curved shape, such as an arc as shown in FIGS. 1-3 which typically is bent into an S-shape to match the anatomy of the throat. In FIGS. 1-3 the printed electrodes are shown on the outer curved surface for receiving electrical signals generated from nerves and muscles in the rear of the trachea. A second embodiment of the laryngeal electromyography tube 40 shown in FIGS. 4 and 5 has the electrodes placed on the concave (inner surface of the curve) for picking up signals generated from the vocal cord located on the front surface of the trachea. FIG. 6 shows a third embodiment of a laryngeal electromyography tube 50 incorporating features of the invention. This embodiment incorporates the electrode plate 14 placement of FIGS. 1-3 with the conductive trace 20 running along the lower surface of the endotracheal tube, the portion of the trace 20 connecting to the plate 14 curving around the surface of the endotracheal tube so that the electrode plate 14 faces rearward to contact the vocal cords and the conductive trace 20 is on the lower surface of the tube as it passes through the mouth (i.e., facing the tongue). One skilled in the art will recognize that other electrode placements may be desired and it may in fact be desirable to have electrodes extending further around the circumference or even around the full 360° circumference of the tracheal tube.

Additional imprinting 26 for informational purposes is applied using nonconductive paint or printing ink is also seen on the body of the invention. An insulating covering 28, shown as a transparent material, is applied over the traces to protect against electrical shorting.

Figure 7:
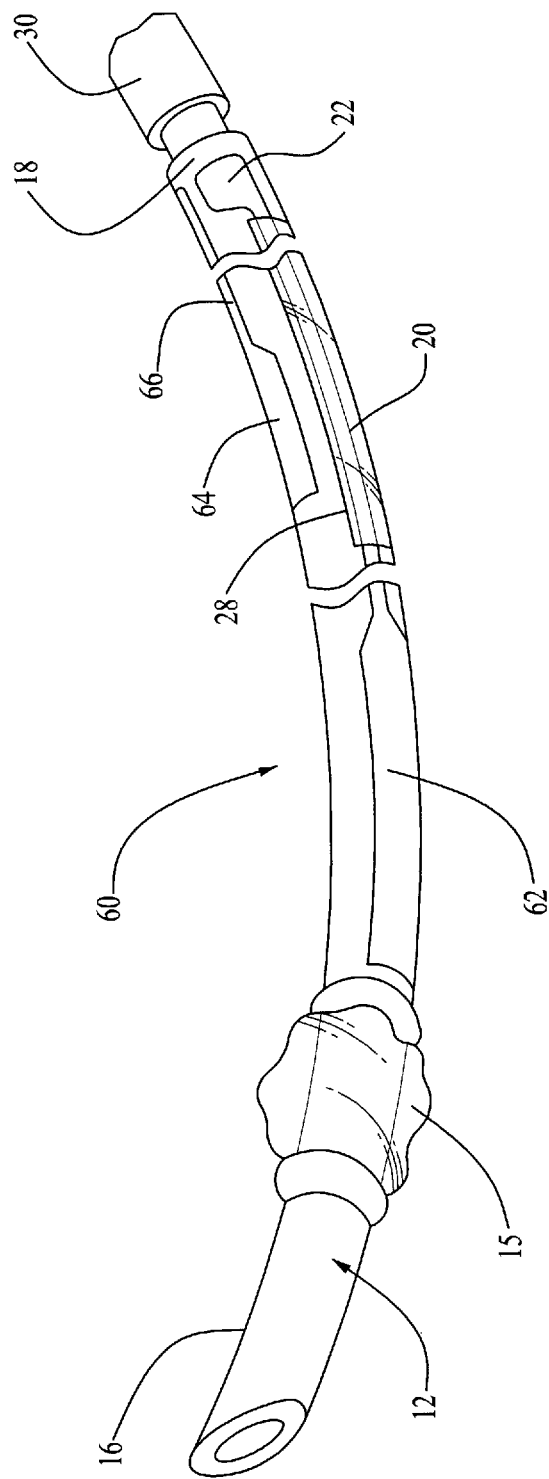
FIG. 7 is a perspective view of a further embodiment of an electrode for prolonged monitoring of laryngeal electromyography incorporating features of the invention.
Figure 8:
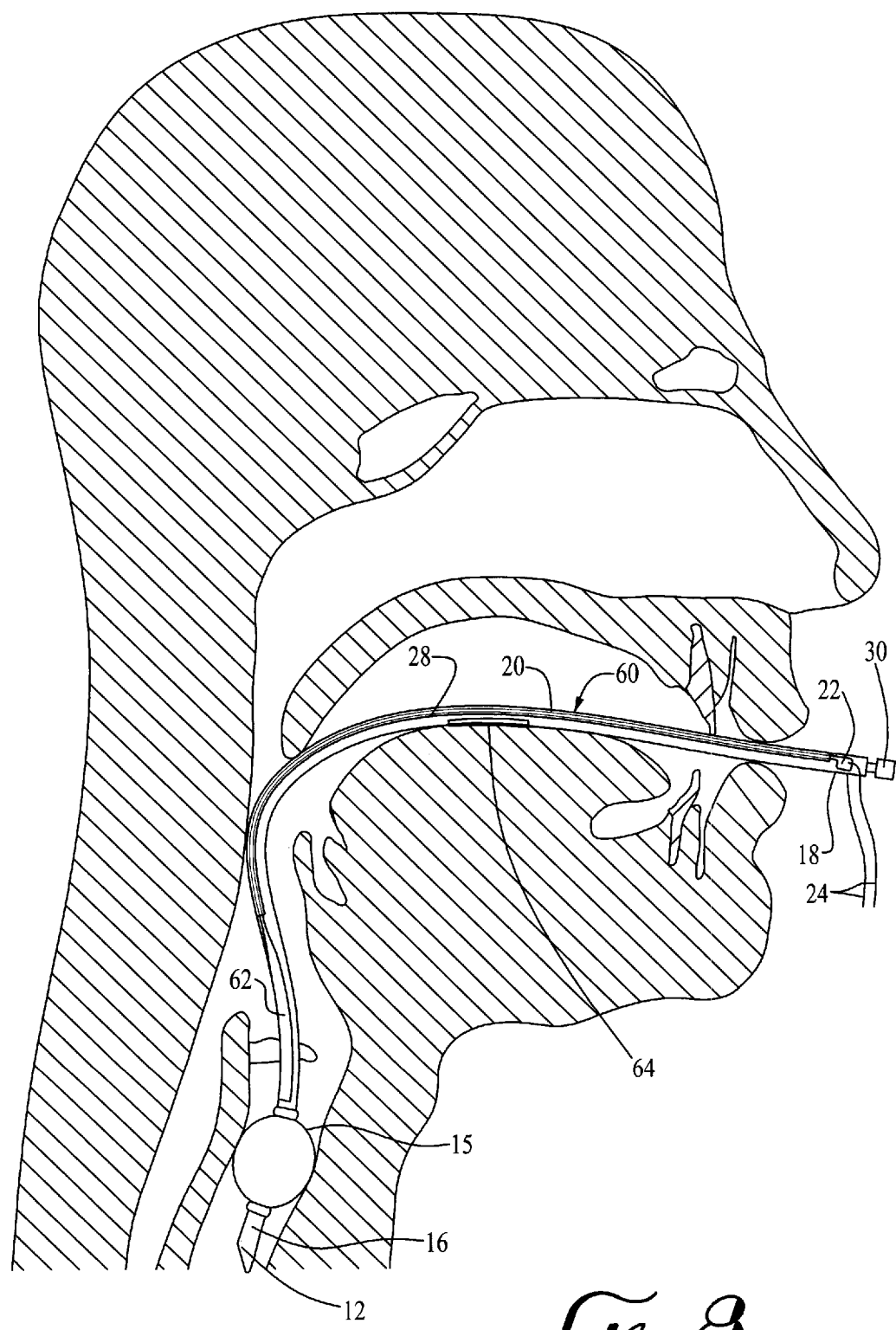
FIG. 8 is a view showing the endotracheal tube of FIG. 7 placed within the trachea with one electrode plate adjacent the vocal cords and one electrode contacting the tongue.

FIGS. 7 and 8 show a still further embodiment 60 which includes a single wide electrode 62 in contact with the vocal cords and a second electrode 64 which rests against the tongue as best shown in FIG. 8. In FIG. 7, a second conductive pad 22 connected to the trace 66 is not seen as it is on the backside of the endotracheal tube as viewed in FIG. 7.

A suitable conductive composition, referred to as an ink or paint, for forming the plates 14 and the traces 20 comprises a mixture of conductive materials, preferably metallic particles or metallic salts or oxides dissolved or suspended in a liquid carrier. Suitable conductive particles include, but are not limited to, finely divided particles or flakes of silver, silver salts such as silver chloride, silver oxide, gold, copper, copper chloride, platinum, carbon or graphite. The conductive materials are provided in the form of pellets, flakes, and nanoparticles. Silver is preferred because it is highly conductive (it has a resistivity of $1.62 \times 10^{-8}$ $\Omega$m), is oxidatively stable and has the added advantage that its oxide is electrically conductive. Copper has a similar resistivity but its oxide acts as an insulator. The conductive materials are dissolved or suspended in a carrier which can be readily evaporated, leaving the conductive particles adhered to the surfaced of the endotracheal tube and in contact with adjacent particles to create a continuous conductive path from the electrode plate 14 along the length of the endotracheal tube to the conductive pad 22 and then to the lead wires 24. A typical ink comprises a mixture of the conductive material, which may include one or more different materials such as silver in combination with silver chloride, in a liquid carrier, and may also include a binding agent or adhesion promoter. A typical ink for use on a polyvinyl chloride (PVC) endotracheal tube comprises 20-40% of a liquid carrier and 60-80% of a conductive material blend. For example a particular embodiment for use on PVC comprises 30% of a liquid carrier, such as dipropylene glycol methyl ether, 60% silver in the form of 50% silver flakes and 10% silver chloride, and a resin binder such as a modified polyester resin. Once the liquid carrier is removed, the printed electrode comprises about 85% conductive silver material (silver and silver chloride), the balance being the resin binder. Numerous suitable conductive inks are available from Creative Materials of Tyngsboro, Mass.

For use on a silicone endotracheal tube a preferred carrier liquid is Xylene. The ink typically has a viscosity in excess of 10,000 centipoises, preferably about 12,000-16,000 cps. One skilled in the art will recognize that numerous different carriers can be employed, preferably a liquid that does not attack or dissolve the polymeric material comprising the endotracheal tube and is readily evaporated. For example, other suitable liquid carriers include water, methanol, ethanol, isopropanol, 1-methoxypropanol, butanol, ethylhexyl alcohol, terpineol, ethylene glycol, glycerine, ethyl acetate, butyl acetate, methoxypropyl acetate, carbitol acetate, ethylcarbitol acetate, methylcellosolve, butylcellosolve, diethyl ether, tetrahydrofuran, dioxane, methyl ethyl ketone, acetone, dimethylformamide, 1-methyl-2-pyrrolidone, hexane, heptane, dodecane, paraffin oil, mineral spirit, benzene, toluene, xylene, chloroform, methylene chloride, carbon tetrachloride, acetonitrile and dimethylsulfoxide. The viscosity should also be such that the ink once applied does not flow on the surface of the tube so that the dimensions of the printed or painted electrode can be held with design parameters as to with ands thickness.

To apply the ink to the endotracheal tube the tube can first be wiped with a solvent to remove any oils or foreign materials on the surface. Care must be taken to select a cleaning solvent that is compatible with the polymeric material comprising the endotracheal tube and does not affect the surface of the tube. However, wiping the surface may not be necessary. In a first embodiment the conductive ink is applied using a brush, preferably in an automated manner to assure reproducibility. However, other techniques can be utilized such as spraying or using a roller type applicator or other typical printing techniques. In a preferred embodiment the printed surface is subjected to an elevated temperature (35° C.-140° C.), preferably 100° C.-140° C. for several minutes to quickly evaporate the liquid carrier followed by 12-24 hours exposure in clean environment at ambient temperature. The resultant device is an endotracheal tube with an electrode structure toward the distal end thereof and traces from the electrode structure to the proximal end permanently printed on the outer surface thereof, the traces being electrically insulated. The printed electrode and traces are about 0.001 inches (25 microns) in thickness so that the diameter of the endotracheal tube is substantially unchanged and there are no extraneous intervening materials, such as is present when a stick-on electrode is used, which can lift up or present sharp edges.

A PVC endotracheal tube incorporating an electrode structure painted on the surface in the manner described above using the silver/silver chloride ink described above has been used in patients and provides consistent stimulation delivery (the average minimum current required for stimulation of the RLN is about 0.50 mA) and a measurably and consistent output comparable to current electrodes adhesively secured on endotracheal tubes, such as the Dragonfly® stick-on laryngeal electrode supplied by Neurovision Medical, Inc.

Such a composition can be applied by various methods including but not limited to painting, screen printing, transfer printing, gravure, flexographic or offset printing, as well as inkjet or electrostatic printing methods. The conductive solutions preferably use rapidly evaporating solvents which may be provided with high concentrations of the conductive component and can in fact be provided as a solvent free composition. As an alternative, a polymer doped with conductive additives can be used. In a still further embodiment electrically conductive polymers can be used. Based on the teachings herein one skilled in the art will recognize that other conductive solutions or compositions can be utilized.

Preferred materials for construction of the endotracheal tube are PVC or a silicone polymer, such as Silastic®. However, based on the teachings herein one skilled in the art will recognize that numerous alternative materials may be used to construct the endotracheal tube 12. The non-conductive, insulating covering 28 is chosen to be compatible with the tube 12 material to minimize or eliminate the likelihood of delamination. For example, on a PVC endotracheal tube a PVC insulating covering 28 is preferred. For a silicone endotracheal tube, a silicone insulating covering 28 is preferred. While the device described herein is an endotracheal tube, one skilled in the art will also recognize that other medical devices, such as catheters can be prepared in the same manner to have electrodes on the surface thereof.

The endotracheal tube with imprinted electrode surfaces allows safe, long term intubation and clinical monitoring of human laryngeal electromyographic signals. Prior and currently available devices include structures on the surface of the tube which are raised and can have sharp edges and which can cause injury to the tissue of the throat, larynx and vocal cords. For these reasons, the manufacturers of all currently available laryngeal surface electrodes do not recommend continuous laryngeal electrode placement for monitoring purposes in excess of eight hours. The surgeon and anesthesiologist are therefore required to remove the dedicated endotracheal tube with attached electrode and reintubate the patient with a standard, non-electrode endotracheal tube prior to moving the patient to the recovery room or ICU for prolonged respiratory support. This entails the risk of a separate, second airway manipulation and deprives the physician of valuable information which is provided by prolonged and continuous laryngeal monitoring. Since the currently described device with electrical paths applied directly to the surface of the endotracheal tube are smooth, these hazards are eliminated. The described device can be placed prior to or at the time of the surgical procedure, and it can remain in position in the patient after the procedure (i.e., in the recovery room, ICU and subsequent prolonged respiratory support) with significantly reduced risks of injury to the patient. Intubations in excess of 8 hours and in fact for 24-48 hours (long term intubation) are therefore now possible.

Further, printing the electrode on the surface provides for optimization of the configuration of the electrode plates on the body of the endotracheal tube without introducing stiff attachments or physical additions. As a result no physical stress is placed on the tube that could inhibit easy placement of the tube in the trachea of a human patient.

While specific embodiments are disclosed herein, it is understood that the disclosed embodiments are merely exemplary of the invention that may be embodied in various forms. Specific structural and functional details described herein are not to be interpreted as limiting, but merely exemplary and are a basis for teaching one skilled in the art to practice the invention claimed herein below.

The invention claimed is:

1. A device for use in monitoring electrical signals during laryngeal electromyography comprising:
    an endotracheal tube having a retention balloon at or adjacent a distal end thereof, said tube having on its outer surface one or more electrically conductive electrode plates applied proximal of the balloon directly to the surface of the tube, without the inclusion of a carrier film between the tube surface and the electrode plates,
    said tube having on its surface electrically conductive traces connected to or integral with the electrode plates, the traces applied directly to the tube surface and running along the length of the endotracheal tube to a proximal end thereof,
    conductive pads connected to or integral with the conductive traces, the pads applied directly to the tube surface at the proximal end of the endotracheal tube, and
    electrical leads connected to the pads, said leads adapted to connect to monitoring equipment,
    the electrically conductive traces covered by an insulating material along their length from a point adjacent the electrode plates to a point adjacent the conductive pads
    wherein a first of said electrode plates is located proximal of the balloon and positioned to contact the vocal cords when placed within the trachea and a second electrode plate is located further proximal thereof and positioned to contact the tongue when the first electrode plate is positioned to contact the vocal cords.

2. The device of claim 1 wherein said electrically conductive electrode plates, traces and pads comprise a dried conductive paint or printing ink with a liquid carrier removed therefrom.

3. The device of claim 1 wherein the surface of the conductive electrode plates are substantially flush with the outer surface of the endotracheal tube.

4. A method of forming an electrode bearing endotracheal tube for laryngeal electromyography comprising:
    providing an endotracheal tube having a retaining balloon at a distal end thereof,
    forming on an exterior surface of the endotracheal tube one or more electrode plates, at least one trace attached to each of the one or more electrode plates and a conductive pad attached to a proximal end of the traces, a first of said electrode plates located at the distal end of the endotracheal tube proximal of the retaining balloon, the conductive pad or pads located at a proximal end of the endotracheal tube,
    the electrode plates, traces and electrode pads formed by applying a conductive ink in a liquid carrier to the exterior surface of the endotracheal tube,
    evaporating the liquid carrier to provide an electrically conductive path from the electrode plates to the endotracheal tube proximal end, and
    forming an insulating barrier over the traces, the barrier extending from a point of connection of the traces to the electrode plates to a point of connection of the traces to the electrode pads
    wherein a second electrode plate is located proximal of said first electrode plate, the first electrode plate positioned to contact the vocal cords and the second electrode plate positioned to contact the tongue when properly positioned for performing laryngeal electromyography.

5. The method of claim 4 wherein the conductive ink comprises electrically conductive particles in said liquid carrier.

6. The method of claim 5 wherein electrically conductive particles comprise finely divided particles or flakes of silver, silver compounds including but not limited to silver chloride and silver oxide, gold, copper, copper chloride, platinum, carbon or graphite.

7. The method of claim 5 wherein the conductive particles comprises at least about 60% of the ink.

* * * * *